United States Patent
Cao (10) Patent No.: US 9,706,922 B2
(45) Date of Patent: Jul. 18, 2017

(54) WIRELESS ECG ACQUISITION AND MONITORING DEVICE AND SYSTEM

(71) Applicant: ZANSORS LLC, Tysons, VA (US)

(72) Inventor: Hung Cao, Montreal (CA)

(73) Assignee: ZANSORS LLC, Tysons, VA (US)

( * ) Notice: Subject to any disclaimer, the term of this patent is extended or adjusted under 35 U.S.C. 154(b) by 0 days.

(21) Appl. No.: 14/656,282

(22) Filed: Mar. 12, 2015

(65) Prior Publication Data

US 2015/0257644 A1   Sep. 17, 2015

Related U.S. Application Data

(60) Provisional application No. 61/951,790, filed on Mar. 12, 2014, provisional application No. 61/971,314, filed on Mar. 27, 2014.

(51) Int. Cl.

| A61B 5/0408 | (2006.01) |
| H04Q 9/00 | (2006.01) |
| A61B 5/00 | (2006.01) |
| A61B 5/0205 | (2006.01) |
| A61B 5/021 | (2006.01) |
| A61B 5/0478 | (2006.01) |
| A61B 5/0492 | (2006.01) |
| A61B 5/053 | (2006.01) |
| A61B 5/145 | (2006.01) |

(52) U.S. Cl.
CPC ........ *A61B 5/0006* (2013.01); *A61B 5/04085* (2013.01); *A61B 5/725* (2013.01); *H04Q 9/00* (2013.01); *A61B 5/002* (2013.01); *A61B 5/021* (2013.01); *A61B 5/02055* (2013.01); *A61B 5/0478* (2013.01); *A61B 5/0492* (2013.01); *A61B 5/0531* (2013.01); *A61B 5/14532* (2013.01); *A61B 5/681* (2013.01); *A61B 5/6804* (2013.01); *A61B 5/6831* (2013.01); *A61B 2562/0209* (2013.01); *A61B 2562/04* (2013.01); *A61B 2562/164* (2013.01); *A61B 2562/166* (2013.01); *H04Q 2209/40* (2013.01); *H04Q 2209/47* (2013.01)

(58) Field of Classification Search
CPC . A61B 5/0006; A61B 5/0408; A61B 5/04085; A61B 5/6823; A61B 5/6831; A61B 2562/0208; A61B 2562/04–2562/046
USPC ................................ 600/372, 509, 382–393
See application file for complete search history.

(56) References Cited

U.S. PATENT DOCUMENTS

| 5,876,350 A | 3/1999 | Lo et al. |
| 6,416,471 B1 | 7/2002 | Kumar et al. |

(Continued)

OTHER PUBLICATIONS

International Search Report and Written Opinion from PCT/US2015/020199 mailed Jun. 24, 2015.

*Primary Examiner* — Lee S Cohen
*Assistant Examiner* — Erin M Cardinal
(74) *Attorney, Agent, or Firm* — DLA Piper LLP US (57) ABSTRACT

A wearable device that wirelessly automatically acquires and processes signals indicative of a condition of subject's health. The device is adapted to wirelessly transmit the processed signals and other information to a suitable analytic and/or storage device where the subject's condition can be analyzed and/or stored. The signals could be ECG signals and the condition could be the health of the subject's heart.

18 Claims, 12 Drawing Sheets

(56) References Cited

U.S. PATENT DOCUMENTS

| | | | | |
|---|---|---|---|---|
| 6,622,035 B1* | 9/2003 | Merilainen | | A61B 5/04025 |
| | | | | 600/391 |
| 8,639,319 B2 | 1/2014 | Hugh et al. | | |
| 9,414,758 B1* | 8/2016 | Brockway | | A61B 5/6804 |
| 2003/0050548 A1* | 3/2003 | Schmidt | | A61B 5/04025 |
| | | | | 600/373 |
| 2004/0039254 A1* | 2/2004 | Stivoric | | A61B 5/0205 |
| | | | | 600/300 |
| 2004/0073104 A1* | 4/2004 | Brun del Re | | A61B 5/0408 |
| | | | | 600/372 |
| 2006/0270942 A1* | 11/2006 | McAdams | | A61B 5/0531 |
| | | | | 600/547 |
| 2008/0287770 A1* | 11/2008 | Kurzweil | | A61B 5/0408 |
| | | | | 600/388 |
| 2009/0024017 A1* | 1/2009 | Ruffini | | A61B 5/0408 |
| | | | | 600/395 |
| 2009/0112295 A1* | 4/2009 | Hyde | | A61B 5/0059 |
| | | | | 607/88 |
| 2011/0046461 A1* | 2/2011 | McKenna | | A61B 5/14552 |
| | | | | 600/323 |
| 2011/0054583 A1 | 3/2011 | Litt et al. | | |
| 2012/0323127 A1 | 12/2012 | Boyden et al. | | |
| 2013/0116532 A1* | 5/2013 | Brunner | | A61B 5/0536 |
| | | | | 600/390 |
| 2013/0333094 A1* | 12/2013 | Rogers | | A61B 5/6806 |
| | | | | 2/161.7 |

\* cited by examiner

WIRELESS ECG ACQUISITION AND MONITORING DEVICE AND SYSTEM

CROSS REFERENCE TO RELATED APPLICATIONS

This application claims priority to U.S. Provisional Application Ser. No. 61/951,790, filed Mar. 12, 2014, and U.S. Provisional Application Ser. No. 61/971,314, filed Mar. 27, 2014, the entireties of which are incorporated herein by reference.

FIELD OF THE INVENTION

Embodiments disclosed herein relate to the wireless acquisition and monitoring of one or more health and/or wellness conditions of a subject using, for example, a wearable device. In particular, embodiments disclosed herein relate to a wearable device with onboard electronics for wirelessly acquiring, processing and transmitting electrocardiogram (ECG) signals and data.

BACKGROUND

Myocardial infarction results in irreversible loss of heart tissues or cardiomyocytes. Injured human hearts heal by scarring, which leads to remodeling and subsequently, heart failure. Heart failure remains the leading cause of morbidity and mortality in the US and developed world due to failure to adequately replace lost ventricular myocardium from ischemia-induced infarction. Unlike some fish and amphibians whose hearts can regenerate, adult mammalian cardiomyocytes have a limited capacity to regenerate from ventricular injury.

The progress in stem cell technology recently has enabled a solution by offering enormous availability of human cardiomyocytes derived from embryonic stem cells (ESCs) and induced pluripotent stem cells (iPSCs). Advances in ESCs and iPSCs-derived cardiomyocytes (CMs) have rejuvenated the field of cardiac cell transplantation. However, before stem cell-based technology can be brought to clinical use, there is the challenge that the transplanted tissue consisting of derived cardiomyocytes fails to integrate and synchronize with the host. Studies and methods have been proposed to "train" cardiomyocytes towards maturation and integration, which raises a need to monitor the operation of entire hearts.

There are several methods to assess the myocardium, including imaging techniques (optical imaging, ultrasound, MRI, etc.), patch clamping and protein analysis. Although those above-mentioned approaches could deliver thorough information about the myocardium, they are more about the operation at the cell level and fail to give an overall operation of the heart. Accordingly, there is a need and desire for a quick and easy way to acquire information related to the operation of a subject's heart and to monitor the operation of the subject's heart.

SUMMARY

Embodiments disclosed herein provide a wearable device that wirelessly and automatically acquires and processes signals indicative of a condition of subject's health. The device is adapted to wirelessly transmit the processed signals and other information to a suitable analytic and/or storage device where the subject's condition can be analyzed and/or stored. In one embodiment, the signals are ECG signals and the condition is the health of the subject's heart.

DETAILED DESCRIPTION

In the following detailed description, a plurality of specific details, such as types of materials and dimensions, are set forth in order to provide a thorough understanding of the preferred embodiments discussed below. The details discussed in connection with the preferred embodiments should not be understood to limit the claimed invention. Furthermore, for ease of understanding, certain method steps are delineated as separate steps; however, these steps should not be construed as necessarily distinct nor order dependent in their performance.

To monitor a vertebrate's heart, one can develop an electrode-based technique to continuously obtain electrical phenotype, namely electrocardiogram (ECG). ECG signals with P waves, QRS complexes and T waves contain detailed information about the entire heart's operation. A continuous acquisition of ECG information would enable the applications of monitoring injured and regenerating hearts for diagnosis and prognosis as well as patients with chronic heart diseases.

Figure 1:
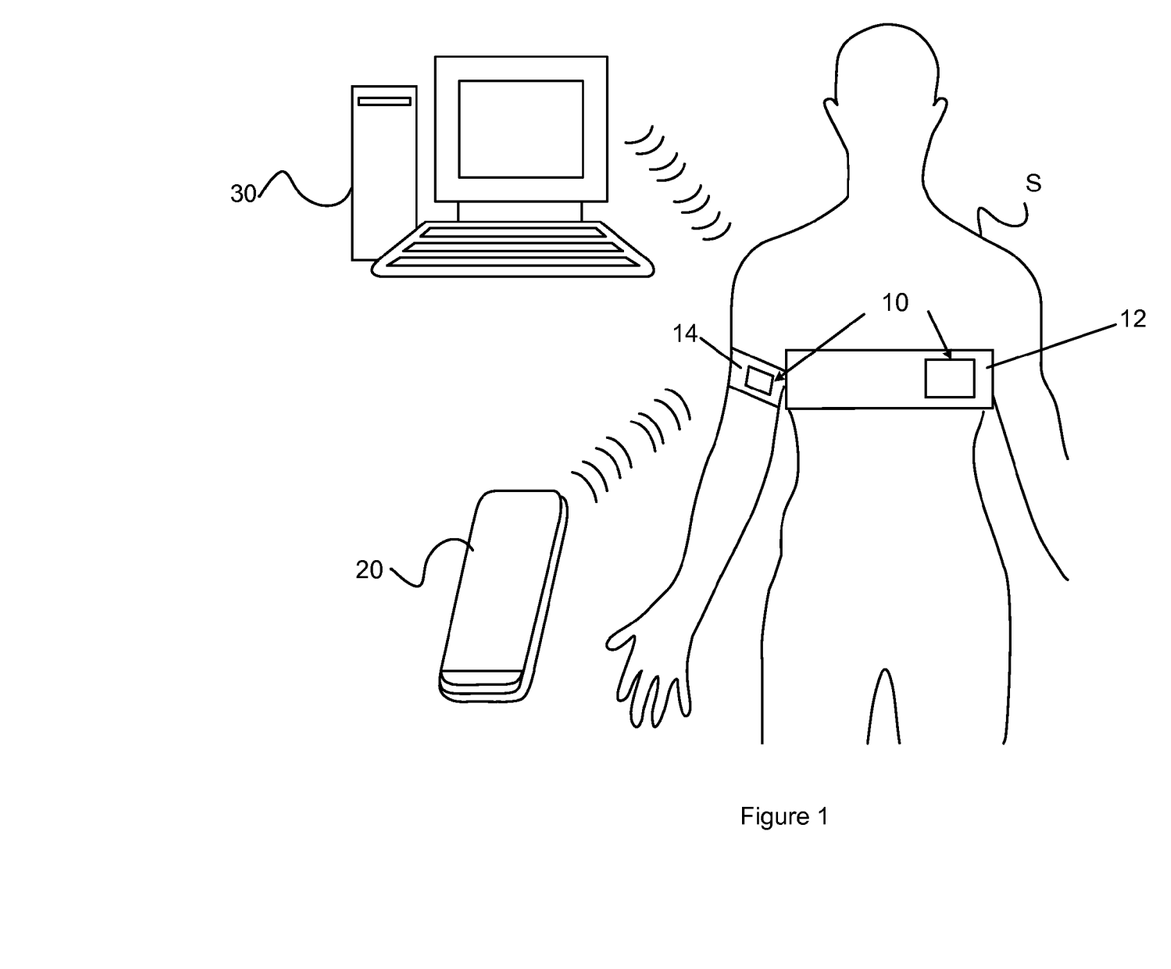
FIG. 1 illustrate examples of a first wearable device disclosed herein being implemented as part of a chest-band and a second wearable device disclosed herein being implemented as part of an arm-band in accordance with the disclosed principles.
Figure 2:
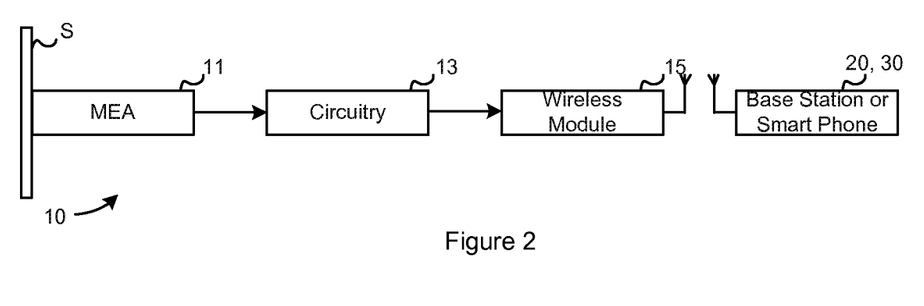
FIG. 2 illustrates in a high-level block diagram form the components of the FIG. 1 device in accordance with the disclosed principles.

In this context, embodiments disclosed herein provide a newly-designed electronic device to be worn by a patient as part of a chest-band or arm-band. Referring to FIGS. 1 and 2, the disclosed device 10 includes a microelectrode array (MEA) membrane 11 that would be placed into contact with a subject's S skin and is used for sensing ECG signals. Electronic circuitry 13 is connected to the MEA 11 to obtain and process the ECG signals. A wireless device 15 is used to transmit the processed signals to a wireless base station 30 (e.g., a computer, laptop, other medical monitoring device) or a smartphone 20 for data analysis and storage. As shown in FIG. 1, the entire device 10 may be embedded in a wearable chest-band 12 or arm-band 14 without any hassle to the subject S. As shown in FIG. 1, the device 10 is adapted to communicate with and transmit signals and information to the subject's S smartphone 20 or a computer 30.

The device 10 disclosed herein offers continuous monitoring of ECG for cardiac patients as well as subjects who want to be examined regularly without the hassles of traditional wired ECG testing. It should be appreciated that other physiological information such as e.g., blood pressure, temperature and blood glucose sensing can be integrated into the device 10, by adding only the sensor elements enabling multi-modality 24/7 monitoring while, at the same time, retaining daily activities of users. It should also be appreciated that a similar device can be embedded into a shirt, pants, headband or helmet for EEG monitoring and that the embodiments disclosed herein are not to be limited to ECG or implementations within an arm-band or chest-band.

Figure 3:
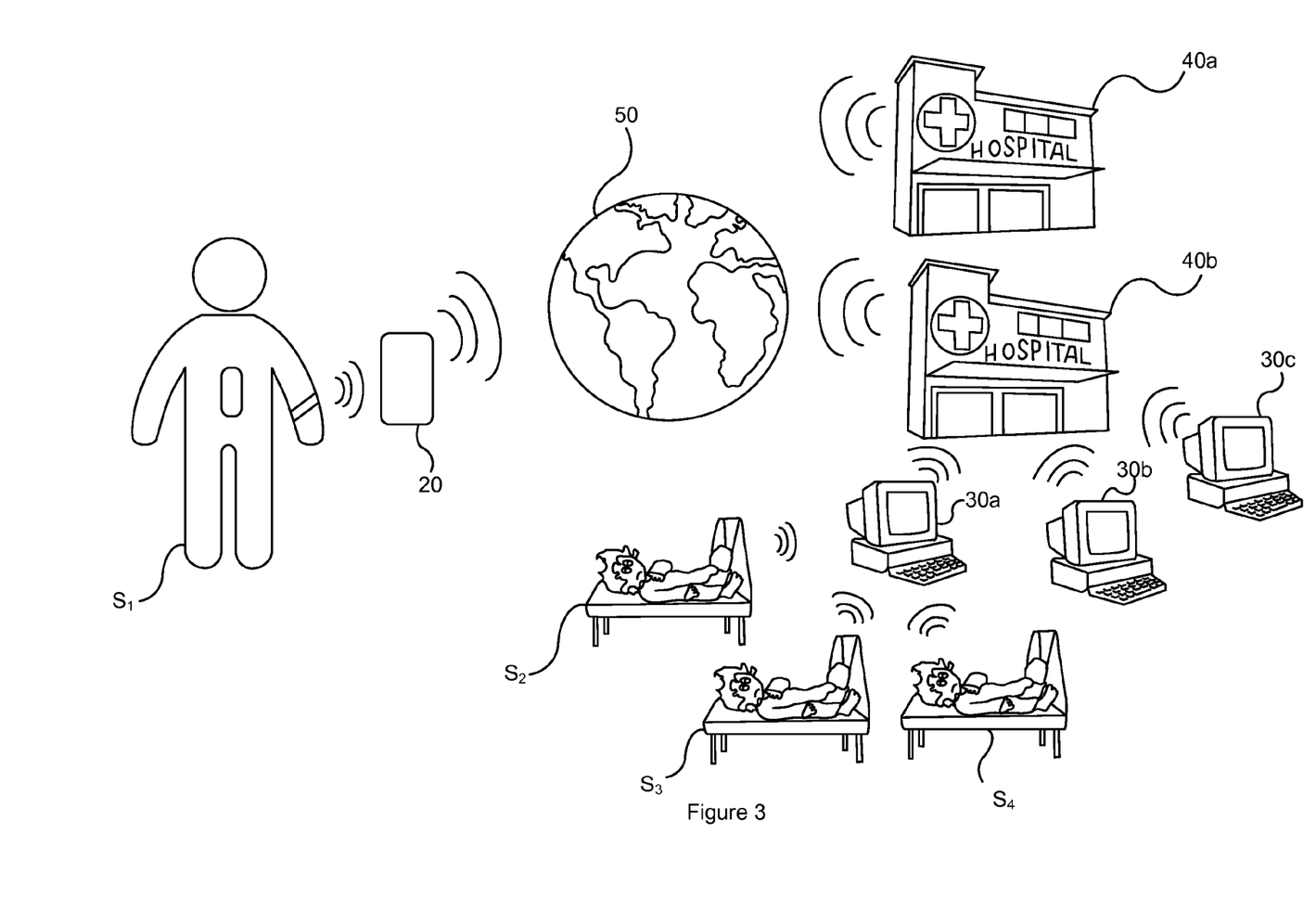
FIG. 3 illustrates the devices of FIG. 1 wirelessly communicating with personal devices, devices associated with hospitals and a mobile health network in accordance with the disclosed principles.

FIG. 3 illustrates the devices 10 of FIG. 1 wirelessly communicating with personal devices (e.g., smartphone 20), devices (e.g., computers 30a, 30b, 30c) associated with hospitals 40a, 40b and a mobile health network 50 in accordance with the disclosed principles. In accordance with the disclosed principles, when the device 10 is worn by a patient $S_2$, $S_3$, $S_4$ in a hospital 40a, 40b, processed data from the device 10 will be sent along with patient identification, which was pre-embedded by e.g., an active Radio Frequency Identification (RFID) tag to a base station (shown as computers 30a, 30b, 30c). For a subject $S_1$ not admitted to a hospital or other medical facility, the device 10 will be customized to send the subject's ECG data to the subject's smartphone 20 or other device (e.g., tablet, laptop, or personal computer). In either scenario, the subjects' $S_1$, $S_2$, $S_3$, $S_4$ data may be shared over the network 50 where it can be stored, further analyzed or shared with other medical or non-medical personnel associated with the network 50.

It should be appreciated that the circuitry/components used by the device 10 to acquire, process and wirelessly transmit the ECG signals/data can be implemented by off-the-shelf components or by a suitably miniaturized ASIC (application-specific integrated circuit). For explanation purposes only, the disclosed embodiments will be described as using off-the-shelf components in accordance with the disclosed principles.

FIGS. 4A-4F illustrate an example fabrication process of a portion of the devices 10 disclosed herein. Specifically, FIGS. 4A-4F illustrate the fabrication of the MEA 11 (FIG. 2). As will be described below, in a desired embodiment, the MEA 11 will be fabricated based on a polymer platform (e.g., parylene C) so that it can conform to the non-planar anatomical surfaces of the subject. The flexibility, stretchability and biocompatibility will guarantee long-term use of the MEA 11 (and thus, the device 10) without signal degradation. In a desired embodiment, the electrical traces of the MEA 11 will be sandwiched between two layers of parylene C.

Figure 4A:
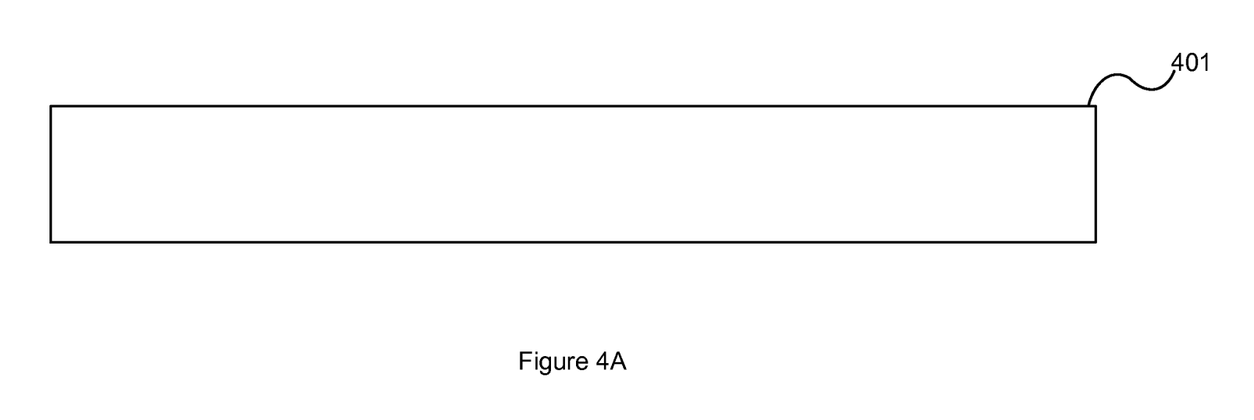
FIGS. 4A-4F illustrate an example fabrication process of a portion of the FIG. 1 devices.
Figure 4B:
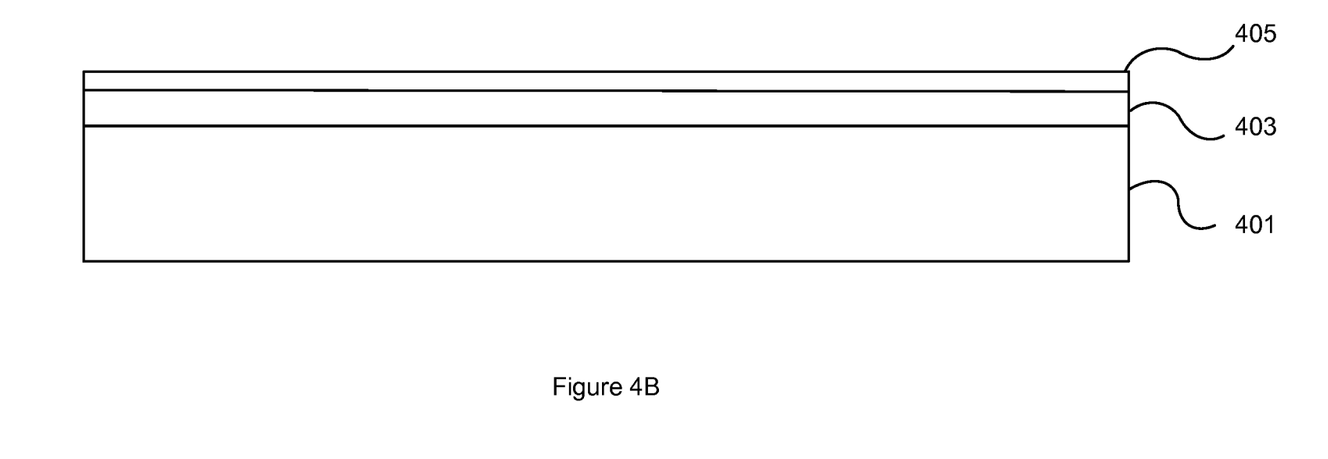
Figure 4C:
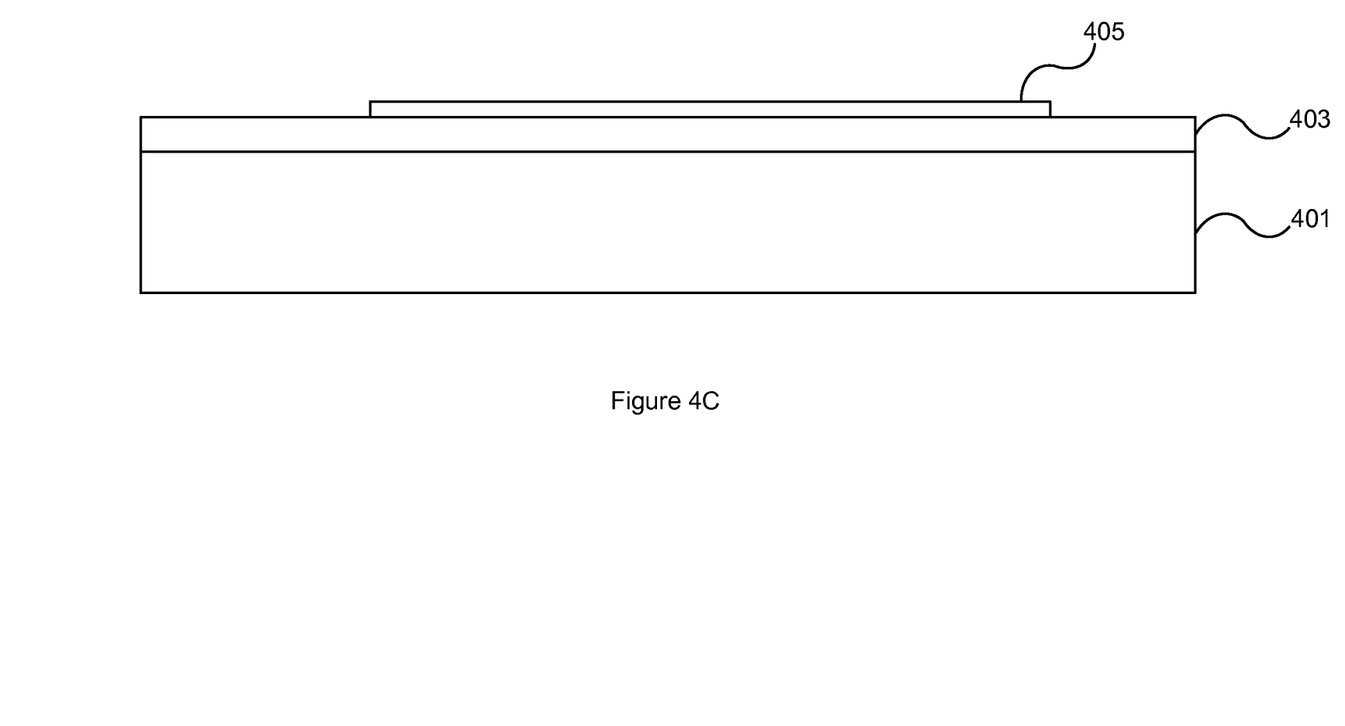
Figure 4D:
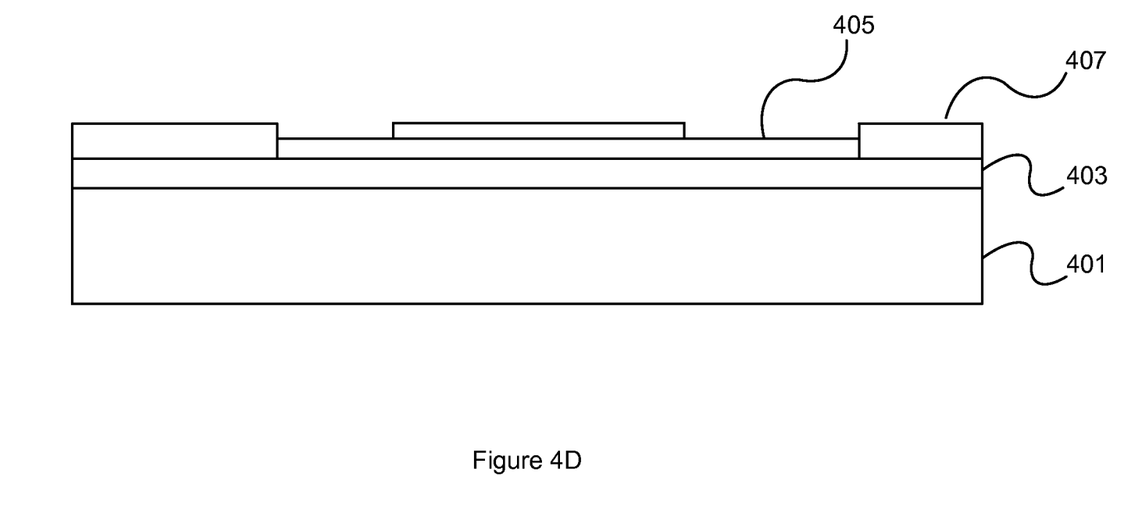

FIG. 4A illustrates a substrate 401 upon which the various layers of the MEA 11 will be fabricated. One desirable substrate 401 includes a silicon wafer, preferably a hexamethyldisilazane-treated (HMDS) silicon wafer. As shown in FIG. 4B, a first parylene C layer 403 is formed over the substrate 401. In one embodiment, the first parylene C layer 403 is deposited onto the substrate 401 and has an approximate thickness of 5 μm. A double layer 405 of gold (Au) and titanium (Ti) is then formed over the first parylene C layer 403. In one embodiment, the titanium is sputtered-deposited to about 0.01 μm thickness and then gold is sputter-deposited to about 0.2 μm thickness. The double layer 405 is then patterned using a gold etchant as shown in FIG. 4C. A second parylene-C layer 407 is formed over the patterned double layer 405 and the first parylene C layer 403. In one embodiment, the second parylene C layer 407 is about 0.5 μm thick. The second parylene C layer 407 is patterned to expose portions of the patterned double layer 405. The exposed portions of the patterned double layer 405 will be used to form electrodes 409 (FIG. 4F) for the MEA 11.

Figure 4E:
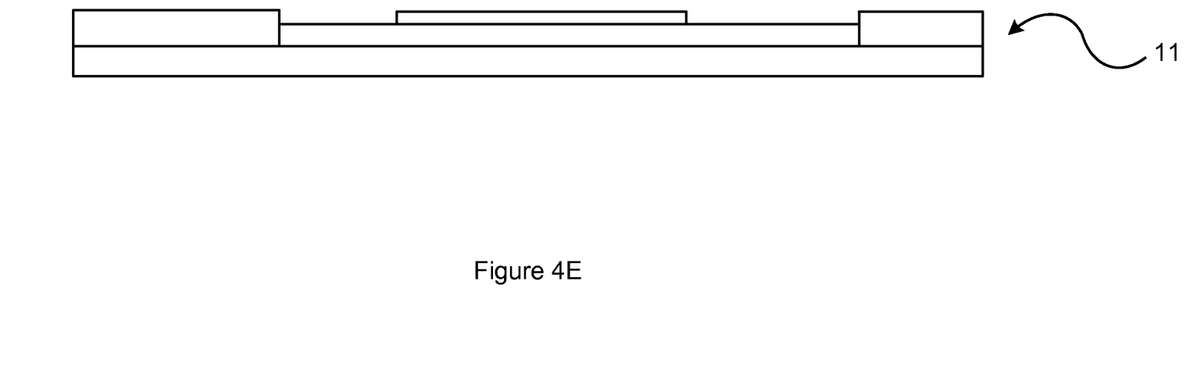
Figure 4F:
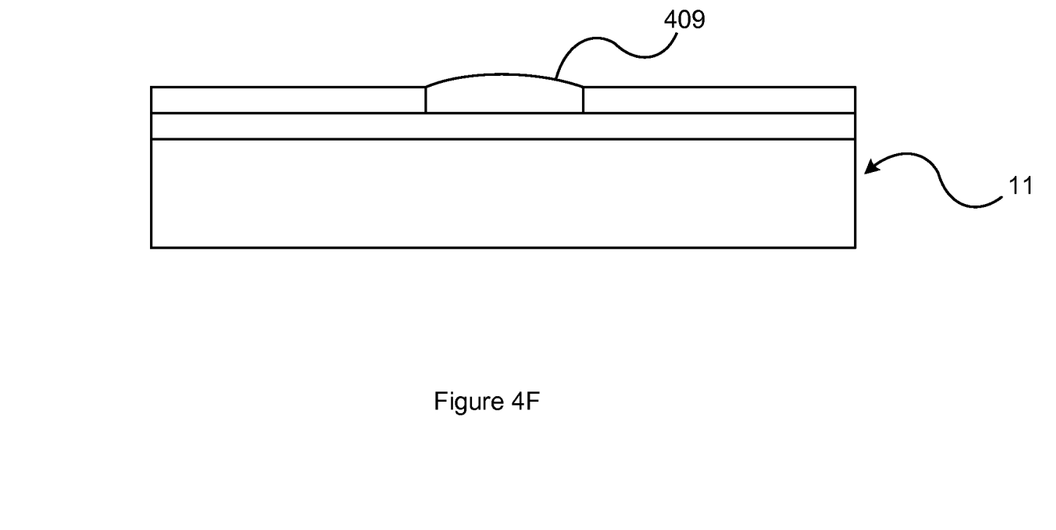

As shown in FIG. 4E, prior to the formation of the electrodes 409, the first parylene C layer 403 will be peeled off the substrate 401, leaving only the layers 403, 405, 407 forming the MEA 11. The exposed portions of the double layer 405 (i.e., electrode areas) will be have additional gold deposited thereon via e.g., electroplating as shown in FIG. 4F. This step provides gold "bumps", which will ensure that there is a good interface between the MEA's electrodes 409 and the subject's skin. In one embodiment, the electrodes 409 and connecting points will be defined by oxygen plasma etching. In one embodiment, the electrode size is approximately 5×5 mm². The number of electrodes 409 can range from three to twelve or more electrodes. It should be noted that twelve electrodes are used in a standard 12-lead ECG often used in medical facilities and clinics. Moreover, it should be appreciated that the disclosed embodiments are not limited to any particular size, length or thickness of the layers/components discussed herein.

Figure 5:
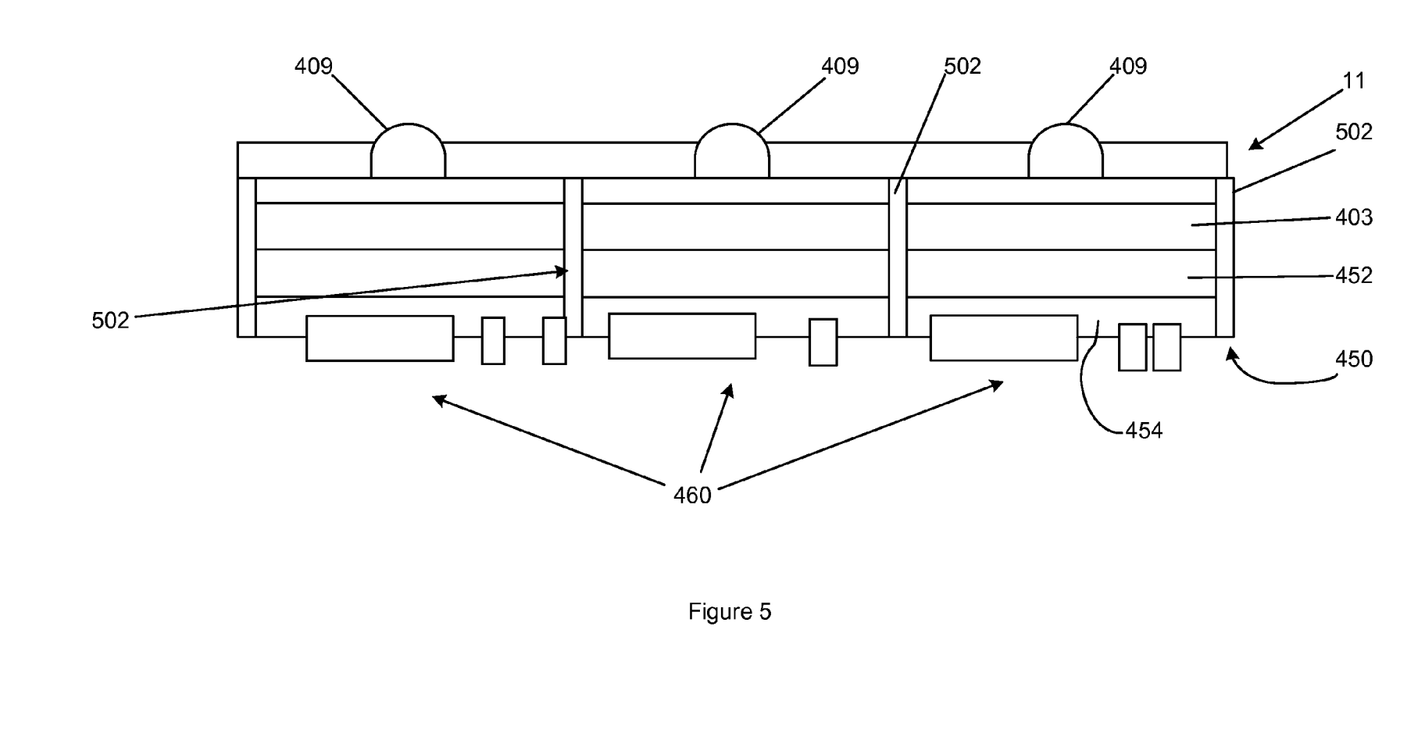
FIG. 5 illustrates a view of an example complete device fabricated in accordance with the disclosed principles.
Figure 6:
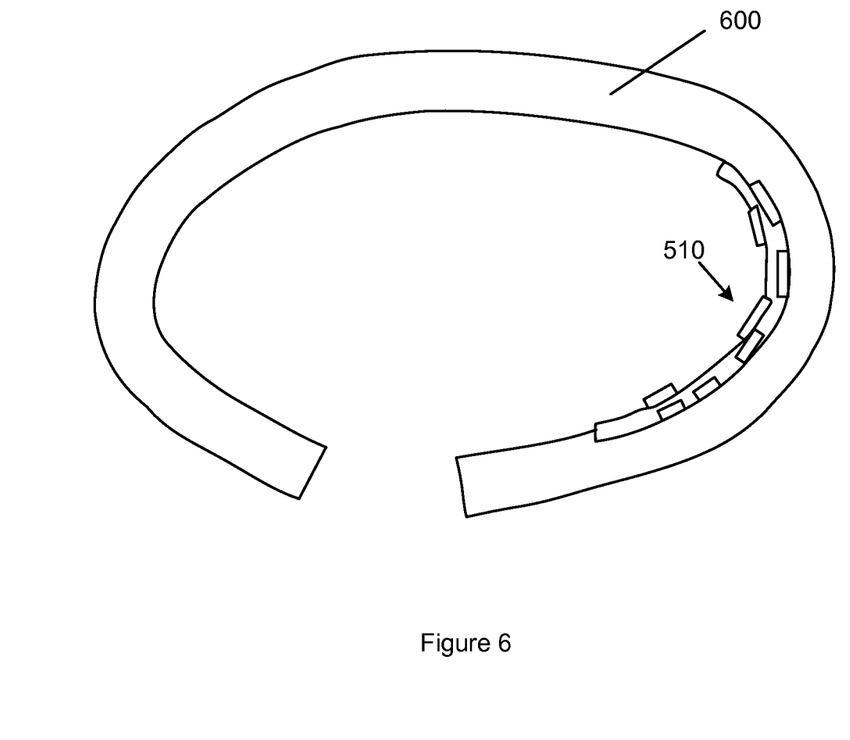
FIG. 6 illustrates the FIG. 5 device implemented as part of a wearable band in accordance with the disclosed principles.

The electronic routing for the circuitry 13 and wireless device 15 of the device 10 will be fabricated using parylene C and the gold/titanium layers using the same processes. For example, as shown in FIG. 5, a circuit portion 450 is fabricated using parylene C layer 452, gold/titanium layer 454 and electronic components 460. The electronic components 460 are discussed below in more detail with reference to FIG. 7. As is also shown in FIG. 5, the first parylene C layer 403 of the MEA 11 is applied to the parylene C layer 452 of the circuit portion 450 (i.e., the two layers of parylene C are attached back-to-back) forming a device 510 (which can be used as the device 10 illustrated in FIGS. 1-3). Conductive-polymer vias 502 are formed through the MEA 11 and circuit portion 450 to connect the electrodes 409 with the electrical components 460. The device 510 will be packaged in flexible and stretchable silicone, which can be embedded safely in a band 600 as shown in FIG. 6.

Figure 7:
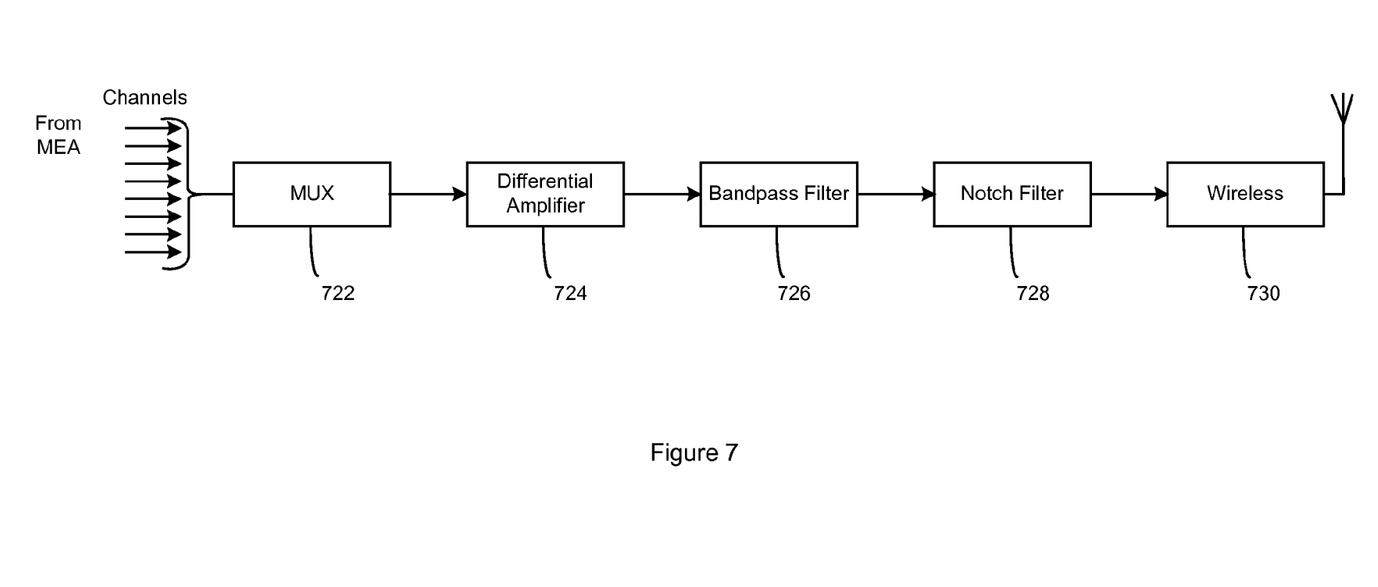
FIG. 7 illustrates in block diagram form the electronic components of the FIG. 5 device constructed in accordance with the disclosed principles.

The electrical components 460 illustrated in FIG. 5 will comprise the electrical circuitry 13 and wireless device 15 of the device 10 illustrated in FIG. 1. Details of that circuitry is illustrated in FIG. 7. As shown in FIG. 7, a multiplexer (MUX) 722 is connected to the electrodes of the MEA 11 and inputs the received signals from the electrodes so that is can combine signals into one output stream. In one embodiment, the multiplexer 722 is a Texas Instrument SN74HC4851 multiplexer chip.

The output of the multiplexer 722 is connected to a differential amplifier 724 that amplifies the original ECG signals. In one embodiment, the differential amplifier 724 is an Analog Devices AD620 amplifier. The differential amplifier 724 is connected to a bandpass filter 726 to filter unwanted signal components and to obtain the desired ECG signals with the frequency in the range of approximately 5-125 Hz. Additionally, a notch filter 728 at 60 Hz is connected to the output of the bandpass filter 726 to remove signal components caused by the power line (i.e., noise). The ECG signals after this circuit should have a distinguishable P waves, QRS complexes and T waves. The output of the filter 726 is sent to a wireless device 730 so that the processed ECG signals can be transmitted from the device to a smartphone, computer, tablet or other suitable device as discussed herein. In one embodiment, the wireless device 730 is a Bluetooth chip (e.g., RN4020 from Microchip Technology).

As noted above, the processing circuitry can be implemented using SMD discrete components, integrated circuits and/or an ASIC. Although not shown, a rechargeable battery will be used to power the circuitry. In one embodiment, the battery will be included as part of the device 10. In another embodiment, the battery can be mounted in the band and connected to the device via an appropriate connection.

It should be appreciated that the device and method disclosed herein provides numerous advantages over ECG devices existing today. For example, although numerous wearable healthcare devices have been proposed in the art, they are still not yet widely used due to their lack of reliability and comfort. With the novel design of the disclosed device (e.g., the electrode "bump", back-to-back assembly, flexible and stretchable materials), flexibility, stretchability and durability are achieved, providing a great advantage over existing devices.

In addition, the wireless operation of the device 10 and the analyzing equipment (smartphone, computer, tablet, etc.) eliminates the complicated wiring on patients in a hospital (compared the conventional approaches such as the 12-lead ECG). This also enables the mobile health network of the future and thus reduces labor and transportation costs by e.g., allowing the acquisition of the ECG signals to be performed by a device remote from the analyzing equipment.

It should also be appreciated that the versatile design for chest-bands and arm-bands provides specific advantages as well as specific purposes. The chest-based device outputs signals with better signal-to-noise ratios and clearer features, thus being an ideal choice for cardiac patients needing cautious monitoring. On the other hand, the arm-based device brings comfort and is hassle-free, which targets all subjects.

The disclosed device is suitable for cardiac patients under cardiac repair as well as subjects interested in health monitoring during everyday life. Moreover, it should be appreciated that the electrode design of the disclosed device is also capable of detecting other physiological signals such as EEG or EMG, etc. As noted above, there are integration options for other sensors, such as blood pressure, temperature, impedance, glucose, etc. It should also be appreciated that the device disclosed herein can be integrated into clothing so that its use will be totally hassle-free to the subject.

The signals obtained by the disclosed embodiments can be displayed on the subject's smartphone for real-time and continuous monitoring, sent to a distanced/networked doctor for online or offline diagnosis or processed by an algorithm to predict the subject's health issues. All of which enable personalized medicine, tele-medicine and a mobile health network where subjects are monitored 24 hours a day, 7 days a week while retaining their daily activities.

It should also be appreciated that the disclosed principles can be used for other situations and types of subjects. For example, there is a great need to monitor, among other things, the breathing, blood pressure and ECG of first responders, firefighters, police, etc. The disclosed wearable device can be integrated into or attached (via e.g., Velcro) to the subject's uniform, if desired, or worn as part of an arm-band or chest-band as illustrated in FIG. 1. In addition, the disclosed wearable device can be applied as a patch, arm-band or chest-band to a patient being treated by e.g., paramedics to obtain measurements such as e.g., patient blood pressure or ECG in a wireless manner.

The foregoing examples are provided merely for the purpose of explanation and are in no way to be construed as limiting. While reference to various embodiments is made, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

Additionally, the purpose of the Abstract is to enable the patent office and the public generally, and especially the scientists, engineers and practitioners in the art who are not familiar with patent or legal terms or phraseology, to determine quickly from a cursory inspection the nature of the technical disclosure of the application. The Abstract is not intended to be limiting as to the scope of the present inventions in any way.

What is claimed is:

1. A device for continuously and wirelessly monitoring a condition of a subject, said device comprising:
   a plurality of sensors, said sensors being adapted to contact the subject and sense signals indicative of the condition from the subject, the plurality of sensors comprising a non-invasive microelectrode array including a plurality of electrodes;
   processing circuitry coupled to the sensors, said processing circuitry being adapted to receive and process the sensed signals from the sensors; and
   a wireless transmission device coupled to receive the processed signals from the processing circuitry, said wireless transmission device being adapted to wirelessly transmit the processed signals to an external device,
   wherein the plurality of sensors, processing circuitry, and wireless transmission device are formed in a flexible and stretchable polymer based material comprising a plurality of openings through which the plurality of electrodes protrude from an inside of the polymer based material to an outside of the polymer based material, the polymer based material being embedded in a band configured to be worn by the subject and conform to a surface of the subject without causing signal degradation in the plurality of sensors, processing circuitry, and wireless transmission device.

2. The device of claim 1, wherein the processing circuitry is adapted to amplify the sensed signals.

3. The device of claim 2, wherein the processing circuitry is adapted to filter the amplified signals.

4. The device of claim 1, wherein the processing circuitry comprises:
   a first circuit adapted to receive the sensed signals and combine them into one output stream;
   an amplifier circuit adapted to amplify the output stream; and
   a filter circuit adapted to filter out noise signal components from the amplified output stream.

5. The device of claim 4, wherein the filter circuit comprises:
   a bandpass filter; and
   a notch filter.

6. The device of claim 1, wherein the plurality of sensors are adapted to sense ECG signals and the condition is a health of the subject's heart.

7. The device of claim 1, wherein the wireless transmission device is a Bluetooth wireless transmission device.

8. The device of claim 1, wherein the flexible and stretchable polymer based material comprises parylene C.

9. The device of claim 1, wherein the processing circuitry and wireless transmission device are sandwiched between two layers of the flexible and stretchable polymer based material.

10. A wearable system for continuously and wirelessly monitoring a condition of a subject, said system being worn by the subject and comprising:
  a band to be worn on a portion of the subject's body; and
  a device embedded in said band, said device comprising:
    a plurality of sensors, said sensors being adapted to contact the subject and sense signals indicative of the condition from the subject, said plurality of sensors comprising a non-invasive microelectrode array including a plurality of electrodes;
    processing circuitry coupled to the sensors, said processing circuitry being adapted to receive and process the sensed signals from the sensors; and
    a wireless transmission device coupled to receive the processed signals from the processing circuitry, said wireless transmission device being adapted to wirelessly transmit the processed signals to an external device,
  wherein the plurality of sensors, processing circuitry, and wireless transmission device are formed in a flexible and stretchable polymer based material comprising a plurality of openings through which the plurality of electrodes protrude from an inside of the polymer based material to an outside of the polymer based material, the polymer based material being configured to conform to a surface of the subject without causing signal degradation in the plurality of sensors, processing circuitry, and wireless transmission device.

11. The wearable system of claim 10, wherein the processing circuitry is adapted to amplify the sensed signals and then filter the amplified signals.

12. The wearable system of claim 10, wherein the processing circuitry comprises:
  a first circuit adapted to receive the sensed signals and combine them into one output stream;
  an amplifier circuit adapted to amplify the output stream; and
  a filter circuit adapted to filter out noise signal components from the amplified output stream.

13. The wearable system of claim 10, wherein the plurality of sensors are adapted to sense ECG signals and the condition is a health of the subject's heart.

14. The wearable system of claim 10, wherein the wireless transmission device is a Bluetooth wireless transmission device.

15. The wearable system of claim 10, wherein the flexible and stretchable polymer based material comprises parylene C.

16. The wearable system of claim 10, wherein the processing circuitry and wireless transmission device are sandwiched between two layers of the flexible and stretchable polymer based material.

17. The wearable system of claim 10, wherein the band is integrated within an article of clothing or an accessory.

18. The wearable system of claim 10, wherein the band is configured to be worn around a torso or a limb of the subject.

* * * * *